United States Patent
Yoshitake et al.

(10) Patent No.: US 6,184,407 B1
(45) Date of Patent: Feb. 6, 2001

(54) CARBOSILOXANE DENDRIMERS

(75) Inventors: Makoto Yoshitake; Satoshi Onodera, both of Chiba Prefecture (JP)

(73) Assignee: Dow Corning Toray Silicone Co., Ltd., Tokyo (JP)

( * ) Notice: Under 35 U.S.C. 154(b), the term of this patent shall be extended for 0 days.

(21) Appl. No.: 09/317,529

(22) Filed: May 24, 1999

(30) Foreign Application Priority Data

| May 29, 1998 | (JP) | 10-166423 |
| Jul. 31, 1998 | (JP) | 10-230154 |
| Aug. 27, 1998 | (JP) | 10-257478 |

(51) Int. Cl.$^7$ .................................................. C07F 7/08
(52) U.S. Cl. ............................................... 556/434
(58) Field of Search ................................. 556/434

(56) References Cited

U.S. PATENT DOCUMENTS

| 5,442,083 | * | 8/1995 | Kobayashi | 556/434 |
| 5,548,051 | * | 8/1996 | Michalczyk et al. | 556/434 X |
| 5,929,187 | * | 7/1999 | Yoshitake | 556/434 X |

FOREIGN PATENT DOCUMENTS

| 0 743 313 A2 | 11/1996 | (EP) . |
| 0 866 086 A2 | 9/1998 | (EP) . |
| 7-17981 | 1/1995 | (JP) . |
| 8-311205 | 11/1996 | (JP) . |

OTHER PUBLICATIONS

"Macromolecules." vol. 26, No. 5, Mar. 1993, pp. 963–968.
"Journal of the American Chemical Society." vol. 113, No. 10, May 1991, pp. 4043–4044.
"Doklady Chemistry." vol. 309, Nos. 1–3, pp. 339–342.
"Journal of the American Chemical Society." vol. 112, No. 19, Sep. 1990, pp. 70770–7079.
"Macromolecules." vol. 24, No. 12, Jun. 1991, pp. 3469–3474.
"Macromolecular Rapid Communications." vol. 17, No. 5, May 1996, pp. 283–297.

* cited by examiner

*Primary Examiner*—Paul F. Shaver
(74) *Attorney, Agent, or Firm*—Timothy J. Troy

(57) ABSTRACT

To provide a novel branched siloxane-silalkylene copolymer whose molecule contains a plural number of silicon-bonded hydrogen atoms or silicon-bonded alkoxy groups.

Carbosiloxane dendrimer that contains at least one siloxane unit with the general formula $$X^1 R^1{}_a SiO_{(3-a)/2}$$

{$R^1$ is $C_1$ to $C_{10}$ alkyl or aryl, $a$ is an integer from 0 to 2, and $X^1$ is the silylalkyl group with the following formula at i=1

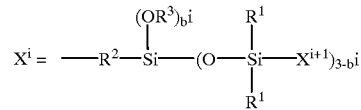

($R^1$ is $C_1$ to $C_{10}$ alkyl or aryl, $R^2$ is $C_2$ to $C_{10}$ alkylene, $R^3$ is $C_1$ to $C_{10}$ alkyl, $X^{i+1}$ is the hydrogen atom or the above-defined silylalkyl group at i=i+1, i is an integer with a value from 1 to 10 that specifies the generation of the said silylalkyl group, and $b^i$ is an integer from 0 to 3 with the proviso that $b^1$ in at least one $X^1$ in each molecule is an integer from 0 to 2)} wherein when more than 1 is present these siloxane units may be the same or different, and whose core is a polysiloxane structure that contains at least 2 silicon atoms and the aforesaid siloxane unit(s).

10 Claims, 5 Drawing Sheets

CARBOSILOXANE DENDRIMERS

FIELD OF THE INVENTION

This invention relates to a novel carbosiloxane dendrimer that has a highly branched structure in which the siloxane bond and silalkylene bond alternate, that contains silicon-bonded hydrogen and/or silicon-bonded-alkoxy, that can also be prepared in a high-molecular-weight form, and that exhibits a narrow molecular weight distribution.

BACKGROUND OF THE INVENTION

Dendrimers are polymers with a narrow molecular weight distribution that have a highly branched structure which elaborates radially from a single core. Dendrimers are characterized by a low viscosity, high reactivity, high solubility, and low glass-transition temperature and as a consequence their applications have been the subject of study. The following are examples of the already known organosilicon dendrimers: siloxane dendrimers (refer to Rebrov et al., *Dokl. Acad. Nauk. SSSR*, 309, 367 (1989) and Masamune et al., *J. Am. Chem. Soc.*, 112, 7077 (1990)), carbosiloxane dendrimers (refer to Kakimoto et al., *Macromolecules*, 24, 3469 (1991); Japanese Published Patent Application (Kokoku or Examined) Number Hei 7-17981 (17,981/1995); and Sheiko et al., *Macromol. Rapid Commun.*, 17, 283 (1996)), and carbosilane dendrimers (refer to Roovers et al., *Macromolecules*, 26, 963 (1993) and Japanese Published Patent Application (Kokoku or Examined) Number Hei 8-311205 (311,205/1996)). This literature also discloses carbosiloxane dendrimers in which the siloxane bond and silalkylene bond occur in alternation (refer to Japanese Published Patent Application (Kokoku or Examined) Number Hei 7-17981 and Sheiko et al., *Macromol. Rapid Commun.*, 17, 283 (1996)). However, the carbosiloxane dendrimers disclosed therein are limited to dendrimers in which the starting reagent that forms the dendrimer core is a silane compound bearing a plural number of vinyl or allyl groups bonded to a single silicon atom, and the methods disclosed therein can only produce low-molecular-weight dendrimer at a low number of generations. The synthesis by a one-step polymerization method of highly branched polymer in which the siloxane bond and silalkylene bond alternate has also been disclosed (refer to Mathias et al., *J. Am. Chem. Soc.*, 113, 4043 (1991)), but this method cannot produce dendrimer with a narrow molecular weight distribution. In sum, then, there has yet to appear carbosiloxane dendrimer that has a highly branched structure in which the siloxane bond and silalkylene bond alternate, that can also be prepared in a high-molecular-weight form, and that exhibits a narrow molecular weight distribution.

Organosilicon polymers containing a plural number of silicon-bonded hydrogen atoms in each molecule are used as crosslinkers in hydrosilylation-based crosslinking reactions and as precursors for the synthesis of functional organosilicon polymers. Desire has recently arisen for the development of novel crosslinkers that can exhibit a high crosslinking efficiency and can generate cured products having excellent properties (e.g., mechanical strength, adhesiveness, and durability) and for the development of novel precursors that would lead to the synthesis of functional organosilicon polymers with unique reactivities. In addition, organosilicon polymers containing a plural number of silicon-bonded alkoxy groups in each molecule are known to be useful as coatings, as starting materials for paint vehicles, and as crosslinkers for moisture-curing compositions. In this case again desire has recently arisen for the development of highly reactive organosilicon polymers that would be useful for improving end-product performance, such as mechanical strength, adhesiveness, and durability. The functional groups bonded at the branch terminals of a dendrimer as a general rule are highly reactive, and in addition a narrow molecular weight distribution can be expected to generate a uniform reactivity. Accordingly, dendrimer bearing the aforementioned reactive groups at its branch terminals would be well-suited for satisfying the desires alluded to above.

The present inventors developed the present invention as a result of extensive investigations directed to solving the problems described above. In specific terms, the object of the present invention is to provide a novel carbosiloxane dendrimer that has a highly branched structure in which the siloxane bond and silalkylene bond alternate and that contains silicon-bonded hydrogen and/or silicon-bonded alkoxy.

SUMMARY OF THE INVENTION

The present invention relates to a carbosiloxane dendrimer that contains at least one siloxane unit with the general formula

where $R^1$ is $C_1$ to $C_{10}$ alkyl or aryl, a is an integer from 0 to 2, and $X^1$ is the silylalkyl group with the following formula at i=1

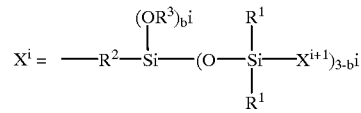

where $R^1$ is $C_1$ to $C_{10}$ alkyl or aryl, $R^2$ is $C_2$ to $C_{10}$ alkylene, $R^3$ is $C_1$ to $C_{10}$ alkyl, $X^{i+1}$ is the hydrogen atom or the above-defined silylalkyl group at i=i+1, i is an integer with a value from 1 to 10 that specifies the generation of said silylalkyl group, and $b^i$ is an integer from 0 to 3 with the proviso that $b^1$ in at least one $X^1$ in each molecule is an integer from 0 to 2 wherein when more than 1 is present the subject siloxane units may be the same or different, and whose core is a polysiloxane structure that contains at least 2 silicon atoms and the aforesaid siloxane unit(s).

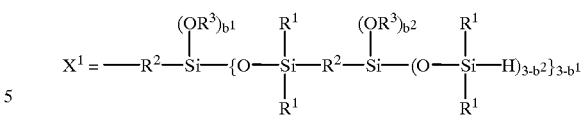

Figure 1:
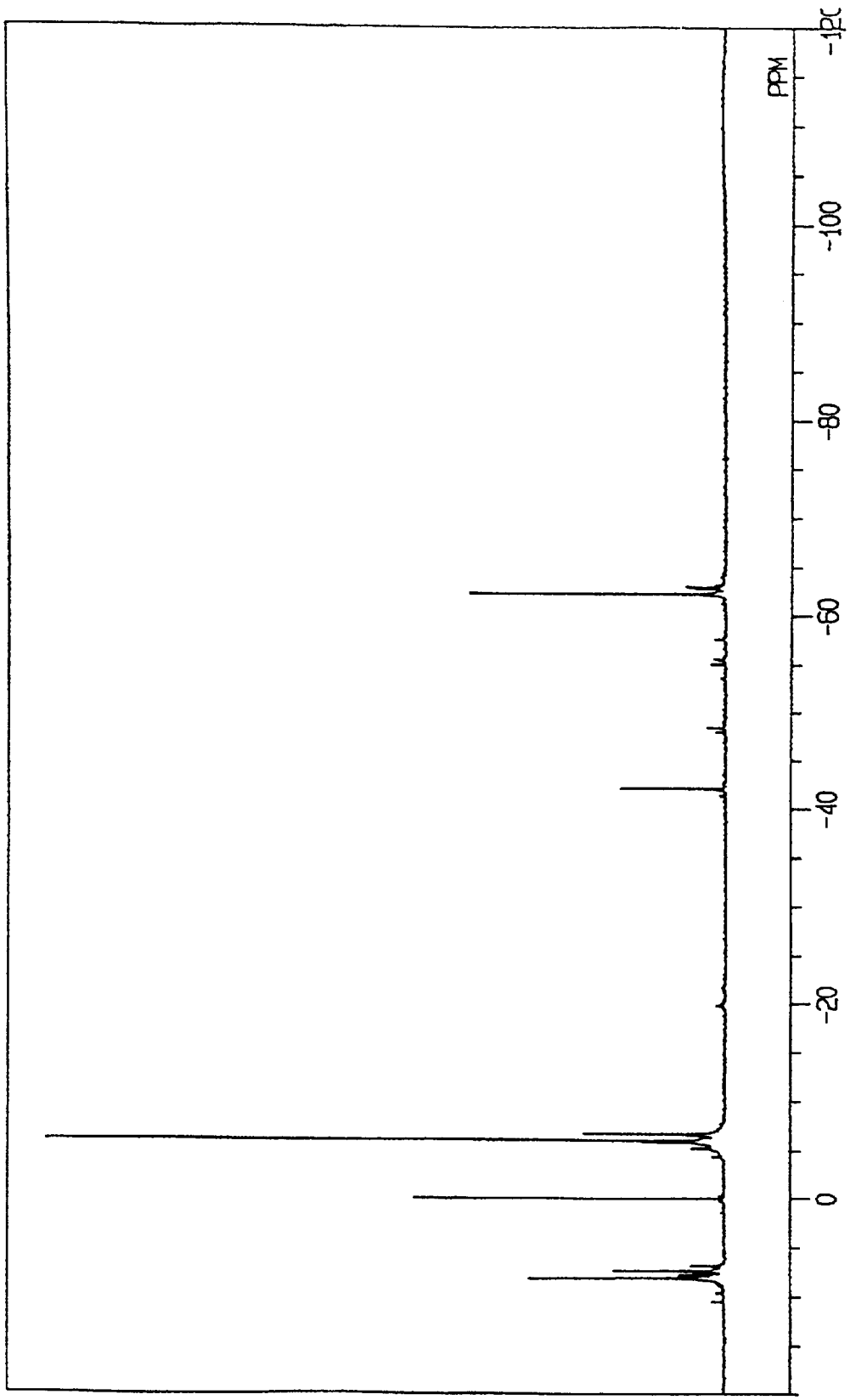
FIG. 1 contains the $^{29}$Si-nuclear magnetic resonance spectrum of the carbosiloxane dendrimer synthesized in Example 1.
Figure 2:
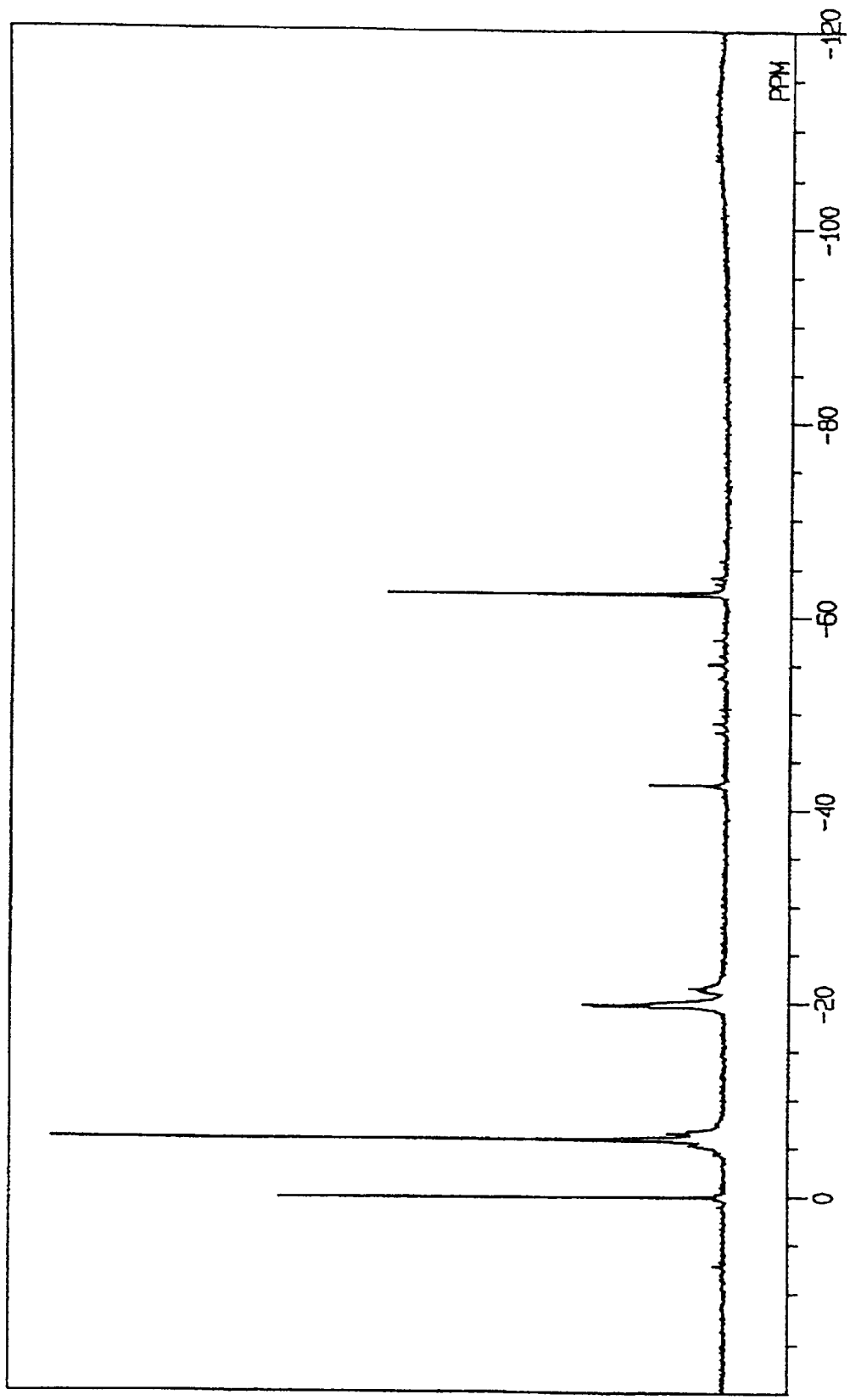
FIG. 2 contains the $^{29}$Si-nuclear magnetic resonance spectrum of the branched carbosiloxane dendrimer synthesized in Example 2.
Figure 3:
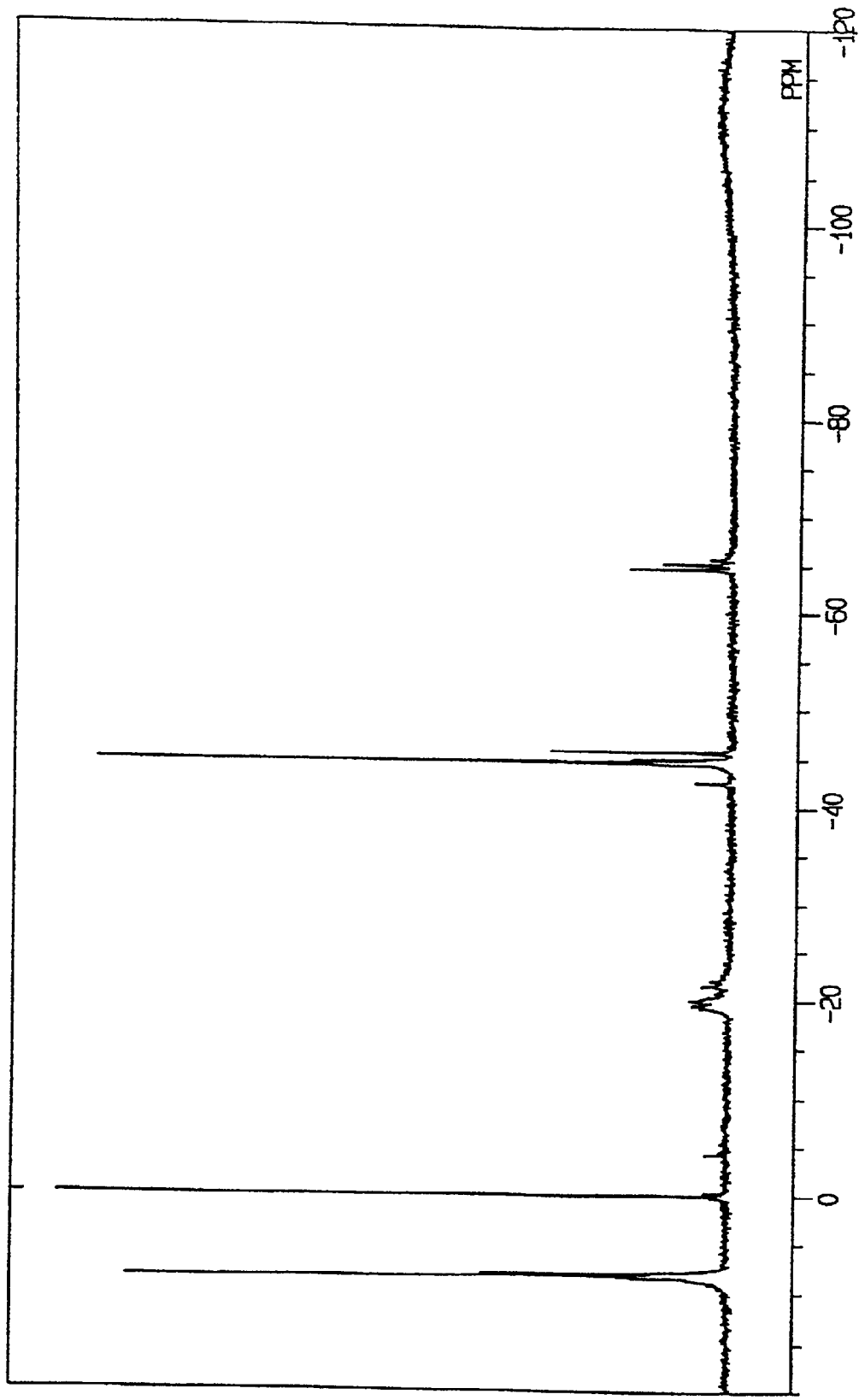
FIG. 3 contains the $^{29}$Si-nuclear magnetic resonance spectrum of the carbosiloxane dendrimer synthesized in Example 3.
Figure 4:
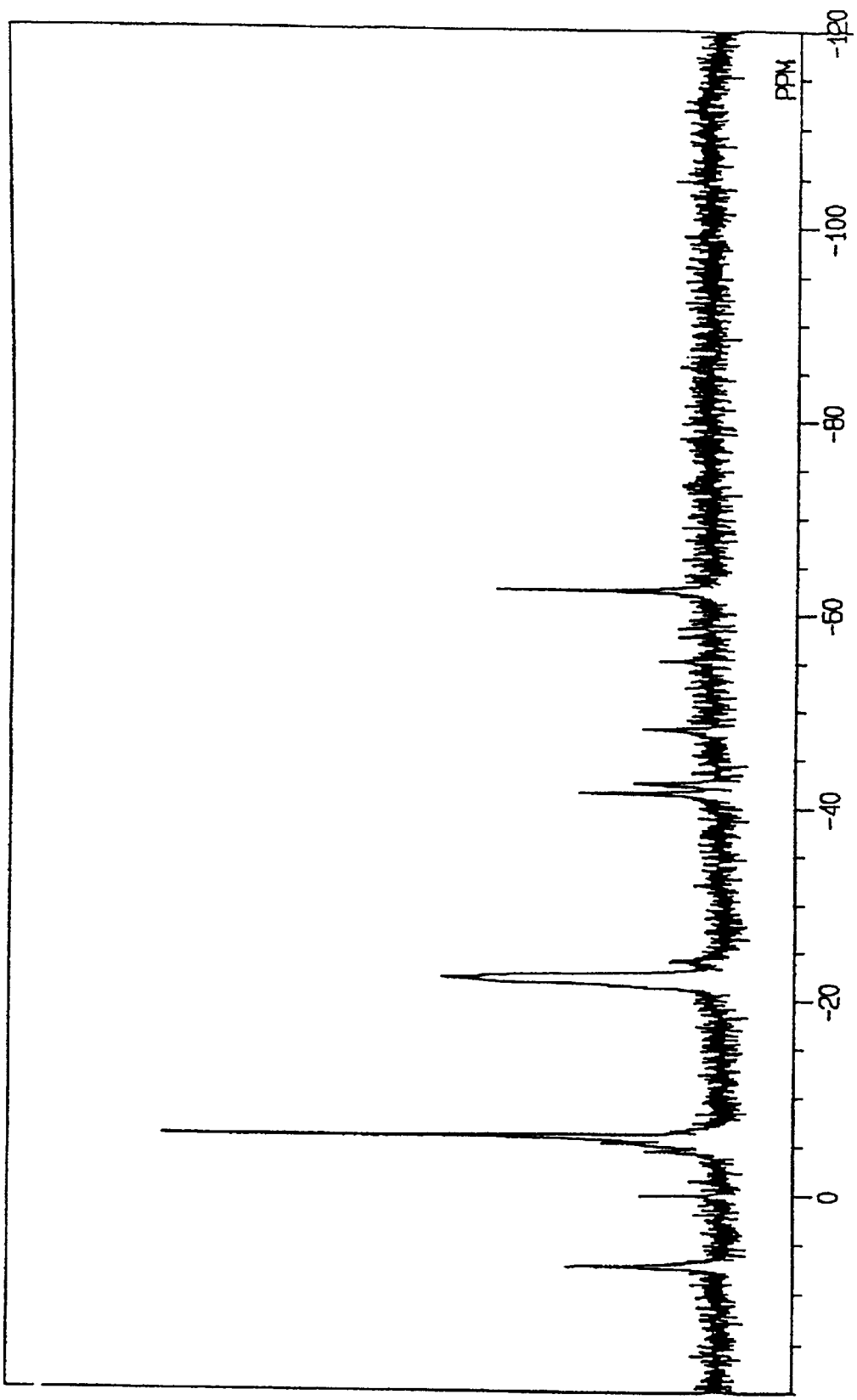
FIG. 4 contains the $^{29}$Si-nuclear magnetic resonance spectrum of the carbosiloxane dendrimer synthesized in Example 4.
Figure 5:
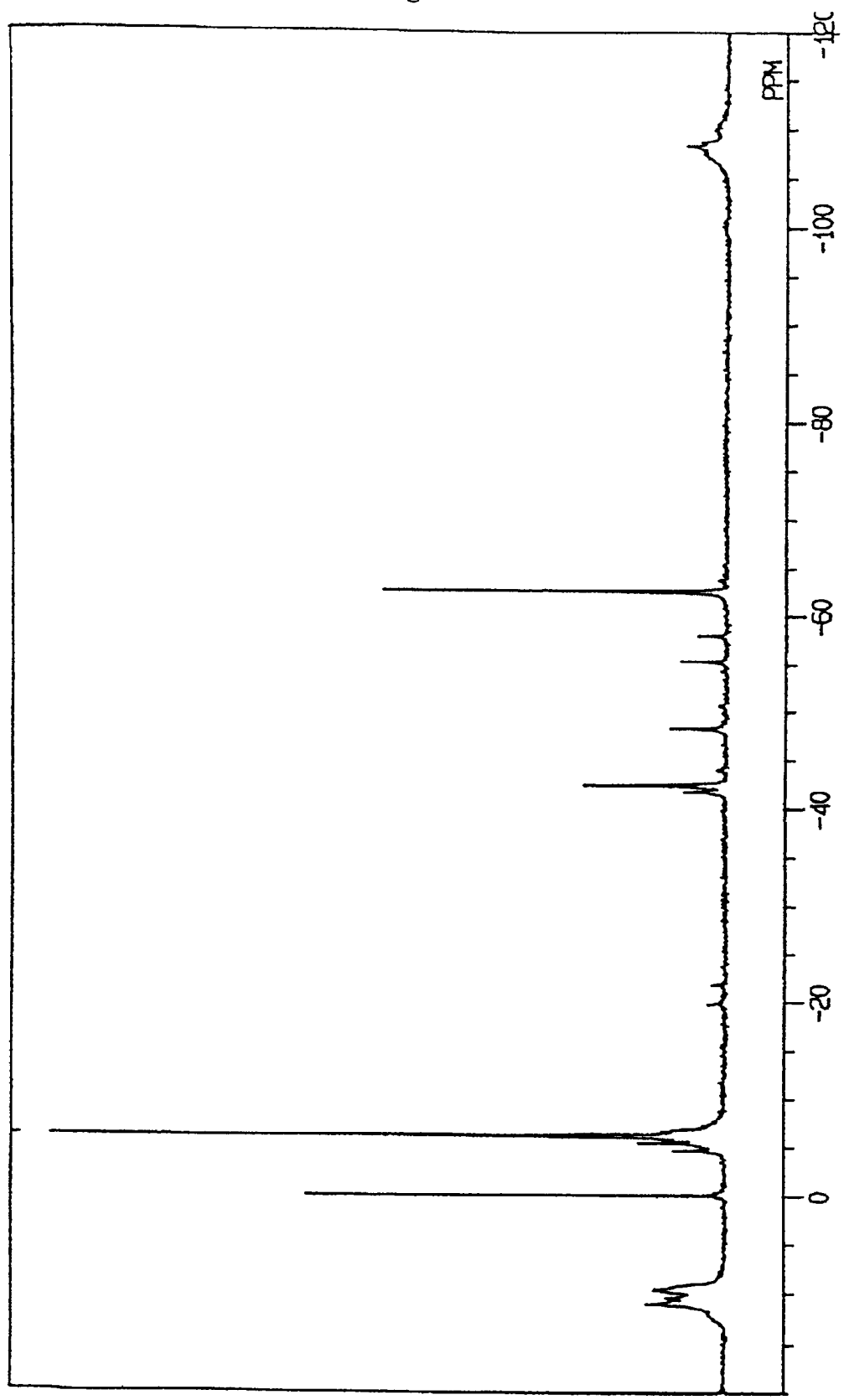
FIG. 5 contains the $^{29}$Si-nuclear magnetic resonance spectrum of the carbosiloxane dendrimer synthesized in Example 5.

and has the following general formula when the number of generations is 3.

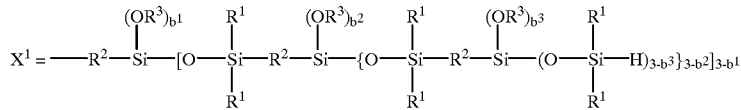

DETAILED DESCRIPTION OF THE INVENTION

The carbosiloxane dendrimer according to the present invention characteristically has a polysiloxane structure that contains at least 2 silicon atoms and at least one siloxane unit with the general formula $X^1R^1_aSiO_{(3-a)/2}$ wherein when more than 1 is present the subject siloxane units may be the same or different. $R^1$ in this general formula is $C_1$ to $C_{10}$ alkyl or aryl. The alkyl encompassed by $R^1$ can be exemplified by methyl, ethyl, propyl, butyl, pentyl, isopropyl, isobutyl, cyclopentyl, and cyclohexyl, while the aryl encompassed by $R^1$ can be exemplified by phenyl and naphthyl. Methyl is preferred among the preceding. The subscript a is an integer with a value from 0 to 2. $X^1$ is the silylalkyl group with the following formula at i=1

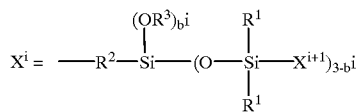

$R^1$ in this general formula is defined as above. $R^2$ in the preceding general formula is $C_2$ to $C_{10}$ alkylene, for example, straight-chain alkylene such as ethylene, propylene, butylene, and hexylene and branched alkylene such as methylmethylene, methylethylene, 1-methylpentylene, and 1,4-dimethylbutylene. Ethylene, methylmethylene, hexylene, 1-methylpentylene, and 1,4-dimethylbutylene are preferred for $R^2$. $R^3$ is $C_1$ to $C_{10}$ alkyl, for example, methyl, ethyl, propyl, butyl, pentyl, and isopropyl, among which methyl and ethyl are preferred. $X^{i+1}$ is the hydrogen atom or the above-defined silylalkyl group. i is an integer from 1 to 10 that indicates the number of generations of the silylalkyl group under consideration, i.e., it indicates the number of repetitions of this silylalkyl group. Thus, this silylalkyl group has the following general formula when the number of generations is 1:

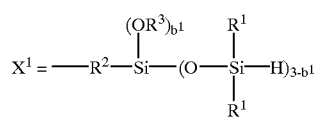

the following general formula when the number of generations is 2:

The polysiloxane structure having at least 2 silicon atoms that is present in carbosiloxane dendrimer according to the present invention must contain at least 1 siloxane unit as represented by the general formula $X^1R^1_aSiO_{(3-a)/2}$ wherein when more than 1 is present the subject siloxane units may be the same or different. The structural units in this organosiloxane comprise monofunctional siloxane units (M units) with the general formulas $X^1R^1_2SiO_{1/2}$ and $R^1_3SiO_{1/2}$, difunctional siloxane units (D units) with the general formulas $X^1R^1SiO_{2/2}$ and $R^1_2SiO_{2/2}$, trifunctional siloxane units (T units) with the general formulas $X^1SiO_{3/2}$ and $R^1SiO_{3/2}$, and the tetrafunctional siloxane unit (Q unit) $SiO_{4/2}$. The following are preferred embodiments of this organopolysiloxane: organopolysiloxane that contains at least one difunctional siloxane unit with the general formula $R^1_2SiO_{2/2}$ or $X^1R^1SiO_{2/2}$ ($R^1$ and $X^1$ are defined as above); organopolysiloxane with the general formula

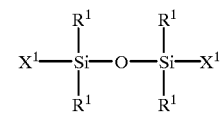

in which $R^1$ and $X^1$ are defined as above; organopolysiloxane that contains at least 5 silicon atoms and is composed of siloxane units selected from the general formulas $R^1SiO_{3/2}$, $X^1SiO_{3/2}$, $R^1_3SiO_{1/2}$, and $X^1R^1_2SiO_{1/2}$ ($R^1$ and $X^1$ are defined as above); and organopolysiloxane that contains at least 6 silicon atoms and is composed of siloxane units selected from the general formulas $SiO_{4/2}$, $R^1_3SiO_{1/2}$, and $X^1R^1_2SiO_{1/2}$ ($R^1$ and $X^1$ are defined as above). The subject organopolysiloxane can be more specifically exemplified by the following general formulas, in which $X^1$ and $R^1$ are defined as above and m, n, x, y, z, p, q, r, s, and t, which denote the number of siloxane units present in each molecule, have values $\geq 1$ wherein $p+q \geq 5$ and $s+t \geq 6$.

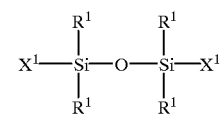

-continued

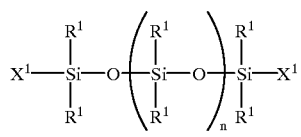

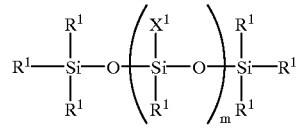

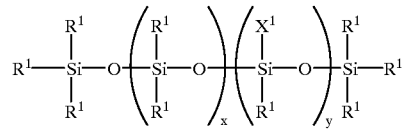

-continued

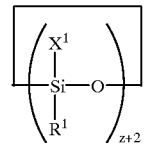

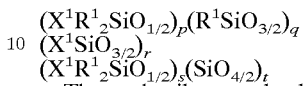

$(X^1SiO_{3/2})_r$
$(X^1R^1{}_2SiO_{1/2})_s(SiO_{4/2})_t$

The carbosiloxane dendrimer according to the present invention can be prepared as a single compound or a mixture of compounds. The dispersity index of the molecular weight (polystyrene basis), that is, weight-average molecular weight/number-average molecular weight ($M_w/M_n$), is preferably $\leq 2$. The subject carbosiloxane dendrimer can be specifically exemplified by polymers with the following average molecular formulas.

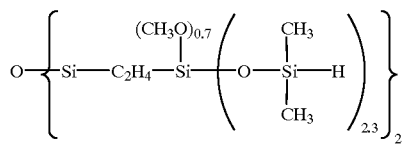

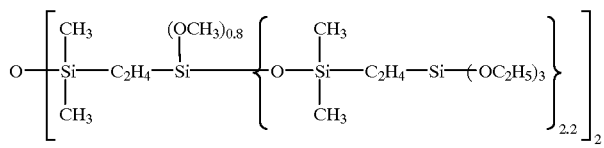

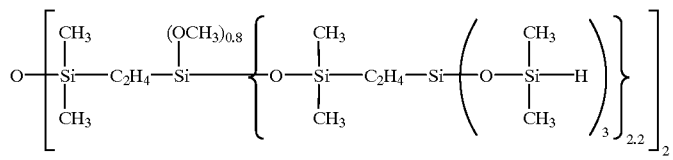

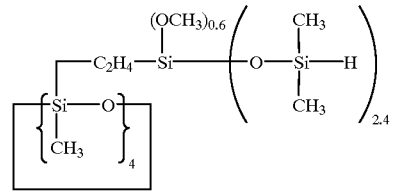

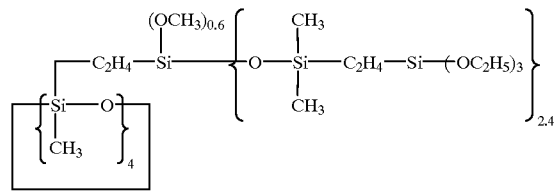

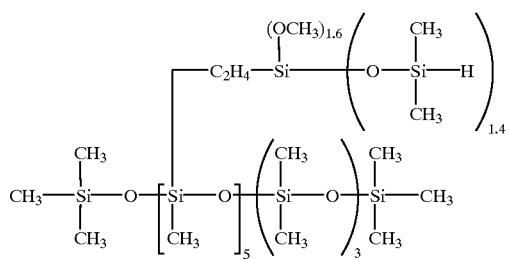

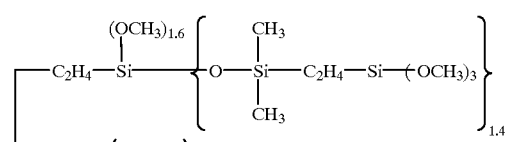

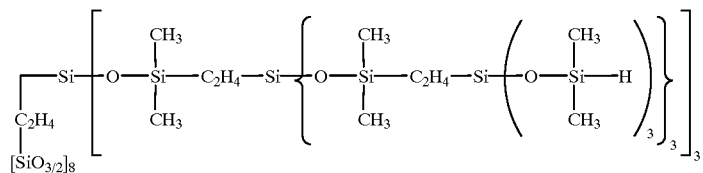

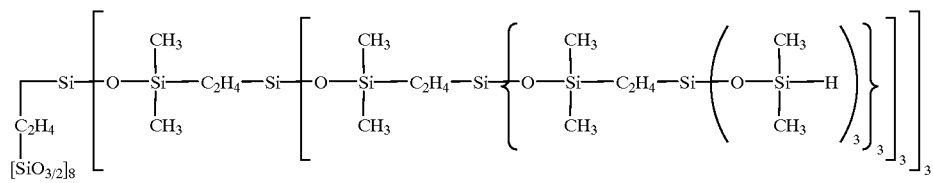

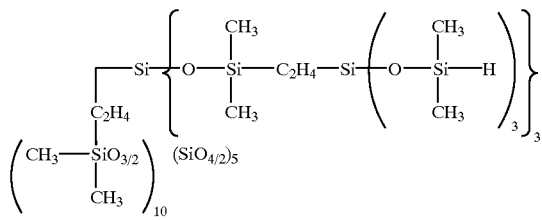

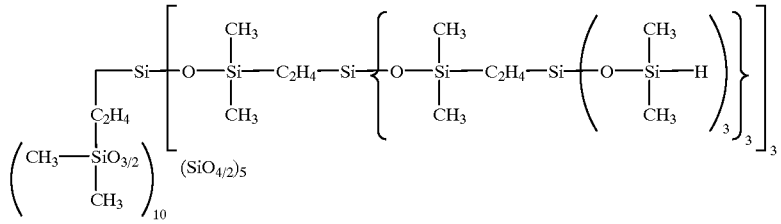

The carbosiloxane dendrimer according to the present invention can be synthesized by executing the following processes (x) and (y) in alternation and at least once each using as starting material an SiH-functional polysiloxane that contains at least 2 silicon atoms and at least one siloxane unit with the general formula $HR^1_a SiO_{(3-a)/2}$ ($R^1$ is $C_1$ to $C_{10}$ alkyl or aryl and a is an integer from 0 to 2) wherein when more than 1 is present the specified siloxane units may be the same or different.

Process (x)

In this process, the aforementioned starting material—or the SiH-functional carbosiloxane dendrimer afforded by the following process (y)—is addition-reacted with alkenyl-functional alkoxysilane with the general formula $R^4Si(OR^3)_3$ ($R^3$ is defined as above and $R^4$ is $C_2$ to $C_{10}$ alkenyl) in the presence of a platinum transition metal catalyst.

Process (y)

In this process, the alkoxy-functional carbosiloxane dendrimer afforded by process (x) is reacted with disiloxane with the general formula

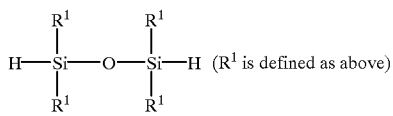

under acidic conditions.

Carbosiloxane dendrimer whose branch terminals are endblocked by alkoxy is obtained when the last step in this preparative method is process (x). Carbosiloxane dendrimer whose branch terminals are endblocked by SiH is obtained when the last step in this preparative method is process (y).

The platinum transition metal catalyst used in process (x) can be exemplified by chloroplatinic acid, alcohol-modified chloroplatinic acid, platinum-olefin complexes, and platinum-diketonate complexes. The platinum transition metal-catalyzed addition reaction is preferably run using a slight excess of the alkenyl-functional alkoxysilane in order to completely react the silicon-bonded hydrogen present in the starting material. After the reaction, the excess alkenyl-functional alkoxysilane can be fractionated off and recovered by, for example, distillation under reduced pressure.

This addition reaction can be run at ambient temperature or with heating and can be run in a solvent that does not inhibit the reaction.

The acid used to produce the acidic condition in process (y) is preferably hydrochloric acid, sulfuric acid, a carboxylic acid, or a sulfonic acid, or a mixture of the preceding. In addition, the silicon-bonded hydrogen is alcoholyzed in process (y) and as a result small amounts of the following monoalkoxysiloxy group may also be present.

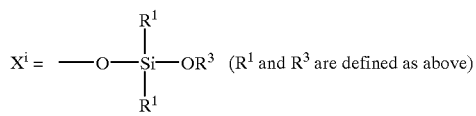

The hereinabove described carbosiloxane dendrimer according to the present invention has the following characteristic features: it has a highly branched structure in which the siloxane bond and the silalkylene bond occur in alternation; it contains silicon-bonded hydrogen and/or silicon-bonded alkoxy; it can also be prepared in a high-molecular-weight form; and it exhibits a narrow molecular weight distribution. Thus, when this carbosiloxane dendrimer contains silicon-bonded hydrogen, it will be useful as a crosslinker for hydrosilylation reaction-curing compositions and as a precursor for functional organosilicon polymers. When, on the other hand, it contains silicon-bonded alkoxy, it will be useful as a coating, as a starting material for paint vehicles, and as a crosslinker for moisture-curable compositions.

The skilled artisan will appreciate that the aforementioned carbosiloxane dendrimers can undergo further reactions, as taught in Japanese Applications 10-257478 and 10-230154, and incorporated herein by reference.

These carbosiloxane dendrimers can be more specifically exemplified by the following average molecular formulae:

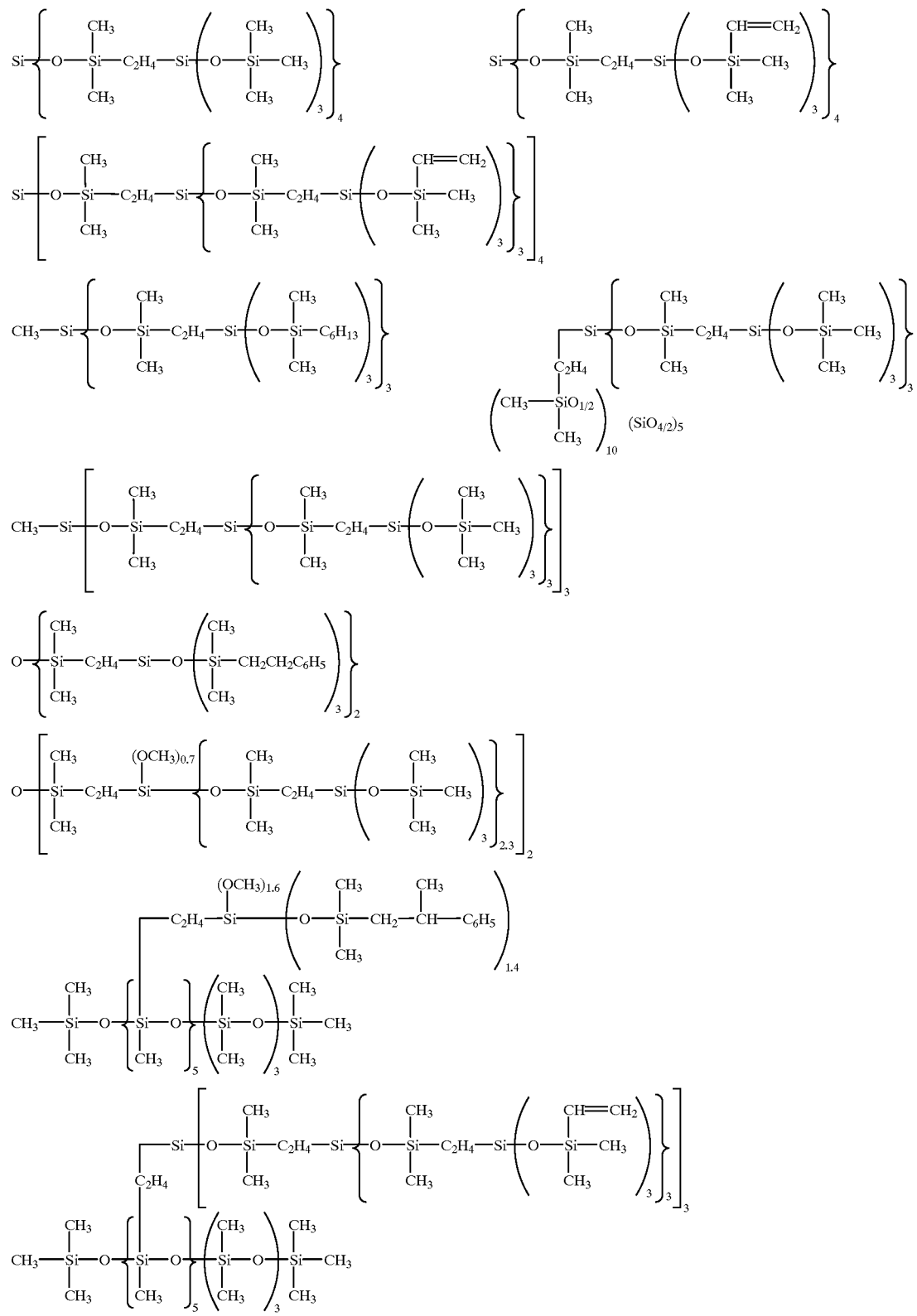

The carbosiloxane dendrimer above can be synthesized, for example, by executing at least one of the following processes (x') through (w'), followed by either process (z') or (w') using as starting material an SiH-functional polysiloxane that contains at least 2 silicon atoms with the general formula $HR^1_a SiO_{(3-a)/2}$ ($R^1$ and $a$ are defined as above). Specifically, it is exemplified that only process (z') is executed, or processes (x') and (y') are executed alternately at least once followed by process (z') after process (y'), or process (x') is conducted followed by process (w').

Process (x')

In this process, the aforementioned starting material—or the SiH-functional carbosiloxane dendrimer afforded by the following process (y)—is addition-reacted with alkenyl-functional alkoxysilane with the general formula $R^4Si(OR^3)_3$ ($R^3$ is defined as above and $R^4$ is $C_2$ to $C_{10}$ alkenyl) in the presence of a platinum transition metal catalyst.

Process (y')

In this process, the alkoxy-functional carbosiloxane dendrimer afforded by process (x') is reacted with disiloxane with the general formula

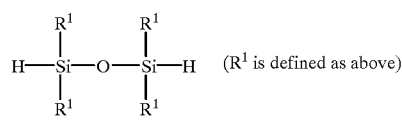

($R^1$ is defined as above)

under acidic conditions.

Process (z')

In this process, the aforementioned starting material—or the SiH-functional carbosiloxane dendrimer afforded by process (y')—is addition-reacted with a compound containing one non-conjugated alkenyl group in the molecule in the presence of a platinum transition metal catalyst.

Process (w')

In this process, the alkoxy-functional carbosiloxane dendrimer afforded by process (x') is reacted under acidic conditions with a disiloxane of the general formula

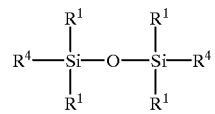

where $R^1$ is defined as above, and $R^4$ is independently a $C_2$ to $C_{30}$ hydrocarbon group.

The platinum transition metal catalyst used in processes (x') and (z') can be exemplified by chloroplatinic acid, alcohol-modified chloroplatinic acid, platinum-olefin complexes, and platinum-diketonate complexes. The platinum transition metal-catalyzed addition reaction is preferably run using a slight excess of the alkenyl-containing compound in order to completely react the silicon-bonded hydrogen present in the starting material. After the reaction, the excess alkenyl-containing compound can be fractionated off and recovered by, for example, distillation under reduced pressure. This addition reaction can be run at ambient temperature or with heating and can be run in a solvent that does not inhibit the reaction. Examples of the alkenyl-containing alkoxysilane used in process (x') include; vinyltrimethoxysilane, vinyltriethoxysilane, hexenyltrimethoxysilane, hexenyltriethoxysilane. Examples of the compound containing one non-conjugated alkenyl group include; butene, isbutene, hexene, octene, styrene, a-methylstyrene, vinyltris(trimethylsiloxy)silane, vinylbis(trimethylsiloxy)silane.

The acid used to produce the acidic condition in processes (y') and (w') is preferably hydrochloric acid, sulfuric acid, a carboxylic acid, or a sulfonic acid, or a mixture of the preceding.

Other carbosiloxane dendrimers can be more specifically exemplified by the following average molecular formulae:

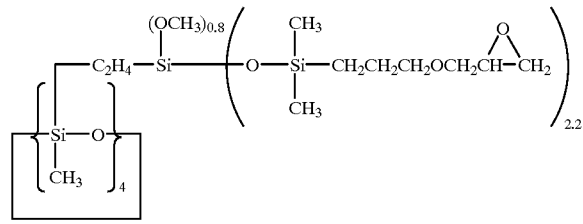

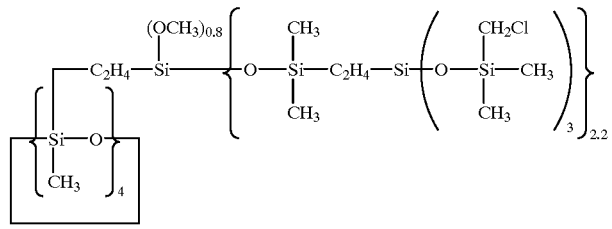

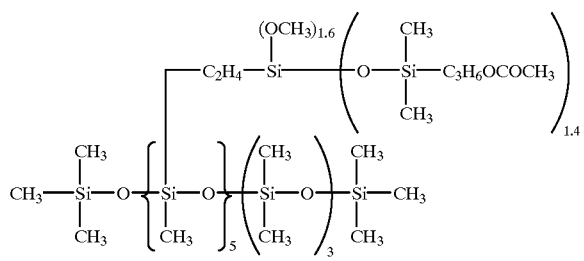

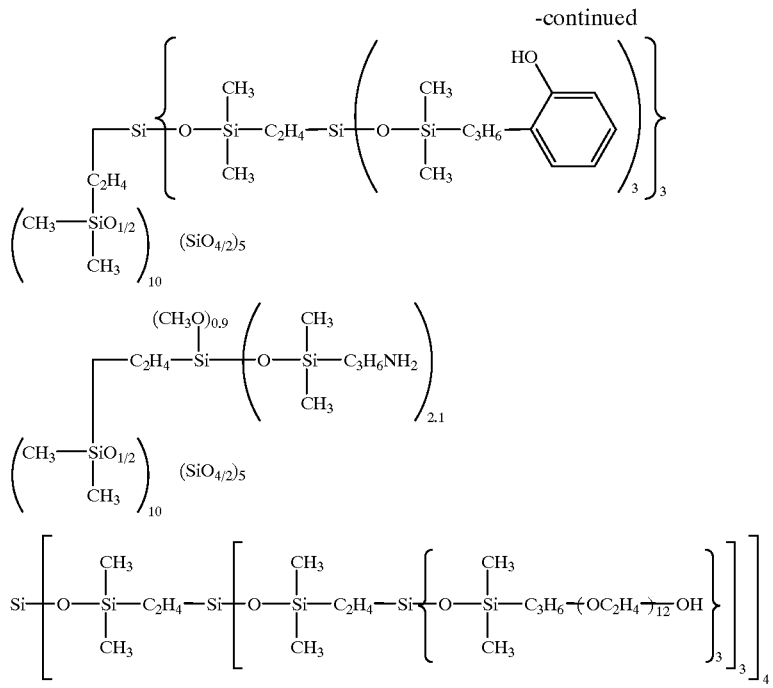

-continued

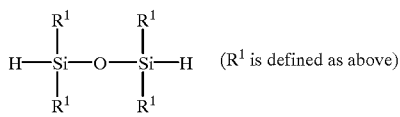

The carbosiloxane dendrimer above can be synthesized, for example, using as starting material an SiH-functional polysiloxane that contains at least 2 silicon atoms with the general formula $HR^1_a SiO_{(3-a)/2}$ ($R^1$ and $a$ are defined as above), by executing either processes (x") and (y") alternately at least once followed by process (z") (only after process (y")), or process (x") followed by process (w").

Process (x")

In this process, the aforementioned starting material—or the SiH-functional carbosiloxane dendrimer afforded by the following process (y")—is addition-reacted with alkenyl-functional alkoxysilane with the general formula $R^4Si(OR^3)_3$ ($R^3$ is defined as above and $R^4$ is $C_2$ to $C_{10}$ alkenyl) in the presence of a platinum transition metal catalyst.

Process (y")

In this process, the alkoxy-functional carbosiloxane dendrimer afforded by process (x") is reacted with disiloxane with the general formula

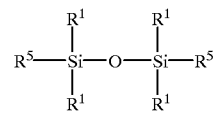  ($R^1$ is defined as above)

under acidic conditions.

Process (z")

In this process, the aforementioned starting material—or the SiH-functional carbosiloxane dendrimer afforded by process (y")—is addition-reacted either with a compound containing one non-conjugated alkenyl group and at least one atom which is different from carbon or hydrogen or a group containing such an atom in the molecule, or a hydrocarbon containing one non-cunjugated alkenyl group per moelcule, in the presence of a platinum transition metal catalyst.

Process (w")

In this process, the alkoxy-functional carbosiloxane dendrimer afforded by process (x") is reacted under acidic conditions with disiloxane having the general formula $$R^5-\underset{\underset{R^1}{|}}{\overset{\overset{R^1}{|}}{Si}}-O-\underset{\underset{R^1}{|}}{\overset{\overset{R^1}{|}}{Si}}-R^5$$

$R^1$ is defined as above, and $R^5$ is an unsubsitituted monovalent hydrocarbon group, a monovalent hydrocarbon group substituted by atoms other than carbon and hydrogen, and a monovalent hydrocarbon group substituted by a group that contains atoms other than carbon and hydrogen.

The platinum transition metal catalyst used in processes (x") and (z") can be exemplified by chloroplatinic acid, alcohol-modified chloroplatinic acid, platinum-olefin complexes, and platinum-diketonate complexes. The platinum transition metal-catalyzed addition reaction is preferably run using a slight excess of the alkenyl-containing compound in order to completely react the silicon-bonded hydrogen present in the starting material. After the reaction, the excess alkenyl-containing compound can be fractionated off and recovered by, for example, distillation under reduced pressure. This addition reaction can be run at ambient temperature or with heating and can be run in a solvent that does not inhibit the reaction. Examples of the alkenyl-containing alkoxysilane used in process (x") include; vinyltrimethoxysilane, vinyltriethoxysilane, hexenyltrimethoxysilane, hexenyltriethoxysilane. The compound, containing one non-conjugated alkenyl group and at least one atom which is different from carbon or hydrogen or a group containing such an atom in the molecule, is preferebly an alkenyl (less than 30 carbon atoms) compound containing at least one group selected from; alcoholic hydroxy, phenolic hydroxy, amino, alkoxy, carboxyl, nitrile, halogen atom, cyclic or acyclil ether-containing, carboxylic ester containing groups. More specifically, examples of such compounds include; allyl alcohol, allyloxyethanol, o-allylphenol, allylamine, butyl allyl ether, undecilenoic acid, allyl cyanate, acrylonitrile, allyl chloride, ally glycidyl ether, allyl methacrylate. The compound with one non-conjugated alkenyl group preferably contains 30 or less carbon atoms. Specific examples include; propylene, 1-butene, isobutene, 1-hexene, 1-octene, styrene, a-methylstyrene.

The acid used to produce the acidic condition in processes (y") and (w") is preferably hydrochloric acid, sulfuric acid, a carboxylic acid, or a sulfonic acid, or a mixture of the preceding.

EXAMPLES

The invention will be explained in greater detail below using working examples, in which the carbosiloxane dendrimer according to the present invention was identified by $^{29}$Si-nuclear magnetic resonance analysis and gel permeation chromatographic analysis (solvent: toluene). (0013)

Example 1

121 g vinyltrimethoxysilane and 0.04 g 3% isopropanolic chloroplatinic acid solution were introduced into a 200-mL four-neck flask equipped with a stirrer, thermometer, reflux condenser, and an addition funnel and then heated to 105° C. while stirring. To this was then gradually added 50 g 1,1,3,3-tetramethyldisiloxane dropwise from the addition funnel so as to maintain the reaction temperature at 100 to 110° C. After completion of the addition, the reaction solution was heated for an additional 1 hour at 115° C. After cooling, the reaction solution was concentrated under reduced pressure to give 158 g of a very light brown liquid. 180 g 1,1,3,3,-tetramethyldisiloxane, 50 mL concentrated hydrochloric acid, 100 mL water, and 100 mL isopropanol were subsequently placed in a 1-liter four-neck flask equipped with a stirrer, thermometer, reflux condenser, and an addition funnel and were stirred. The 158 g of the very light brown liquid prepared as described above was then gradually added dropwise from the addition funnel over 1 hour. After the completion of addition, the reaction solution was stirred at room temperature for an additional 1 hour. The reaction solution was then transferred to a separatory funnel, the lower layer was separated off, and the remaining upper layer solution was washed 3 times with 100 mL water, then once with 100 mL saturated aqueous sodium bicarbonate solution, and finally dried over anhydrous calcium chloride. The solids were filtered off and the resulting solution was concentrated under reduced pressure to yield 233 g of a colorless and transparent liquid. Analysis of this reaction product by $^{29}$Si-nuclear magnetic resonance analysis confirmed it to be carbosiloxane dendrimer with the average molecular formula given below having an average of 4.6 silicon-bonded hydrogen atoms and an average of 1.4 silicon-bonded methoxy groups in each molecule. Using gel permeation chromatography, this carbosiloxane dendrimer was found to have a number-average molecular weight of 1,039 (polystyrene basis) and a dispersity index of 1.08.

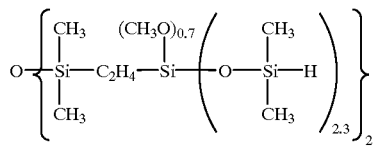

Example 2

88.9 g vinyltrimethoxysilane and 0.04 g 3% isopropanolic chloroplatinic acid solution were introduced into a 200-mL four-neck flask equipped with a stirrer, thermometer, reflux condenser, and an addition funnel and then heated to 100° C. while stirring. To this was then gradually added 30.0 g 1,3,5,7-tetramethylcyclotetrasiloxane dropwise from the addition funnel so as to maintain the reaction temperature at 100 to 110° C. After completion of the addition, the reaction solution was heated for an additional 1 hour at 120° C. After cooling, the reaction solution was concentrated under reduced pressure to give 100.4 g of a very light brown liquid. 93.0 g 1,1,3,3,-tetramethyldisiloxane, 30 mL concentrated hydrochloric acid, 60 mL water, and 60 mL isopropanol were subsequently placed in a 1-liter four-neck flask equipped with a stirrer, thermometer, reflux condenser, and an addition funnel and were stirred. 80.0 g of the very light brown liquid prepared as described above was then gradually added dropwise from the addition funnel over 1 hour. After the completion of addition, the reaction solution was stirred at room temperature for an additional 1 hour. The reaction solution was then transferred to a separatory funnel, the lower layer was separated off, and the remaining upper layer solution was washed twice with 100 mL water, then once with 100 mL saturated aqueous sodium bicarbonate solution, and finally dried over anhydrous sodium sulfate. The solids were filtered off and the resulting solution was concentrated under reduced pressure to yield 98.5 g of a colorless and transparent liquid. Analysis of this reaction product by $^{29}$Si-nuclear magnetic resonance analysis confirmed it to be carbosiloxane dendrimer with the average molecular formula given below having an average of 9.6 silicon-bonded hydrogen atoms and an average of 2.4 silicon-bonded methoxy groups in each molecule. Using gel permeation chromatography, this carbosiloxane dendrimer was found to have a number-average molecular weight of 1,819 (polystyrene basis) and a dispersity index of 1.15.

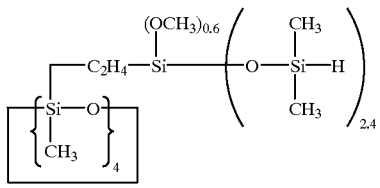

Example 3

54.3 g vinyltriethoxysilane and 0.04 g 3% isopropanolic chloroplatinic acid solution were introduced into a 100-mL three-neck flask equipped with a stirrer, thermometer, reflux condenser, and an addition funnel and then heated to 100° C. while stirring. 27.0 g of the carbosiloxane dendrimer synthesized in Example 2 was then gradually added dropwise from the addition funnel so as to maintain the reaction temperature at 100 to 110° C. After completion of the addition, the reaction solution was heated for an additional 1 hour at 120° C. After cooling, the reaction solution was concentrated under reduced pressure to give 61.9 g of a very light brown liquid. Analysis of this reaction product by $^{29}$Si-nuclear magnetic resonance analysis confirmed it to be carbosiloxane dendrimer with the average molecular formula given below having an average of 29 silicon-bonded ethoxy groups and an average of 2.4 silicon-bonded methoxy groups in each molecule. Using gel permeation chromatography, this carbosiloxane dendrimer was found to have a number-average molecular weight of 3,690 (polystyrene basis) and a dispersity index of 1.17.

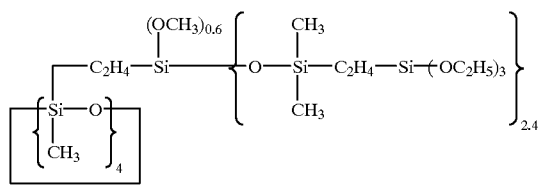

Example 4

49.4 g vinyltrimethoxysilane and 0.04 g 3% isopropanolic chloroplatinic acid solution were introduced into a 100-mL three-neck flask equipped with a stirrer, thermometer, reflux condenser, and an addition funnel and then heated to 100° C. while stirring. 30.0 g polysiloxane with the following average formula

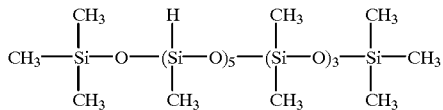

was then gradually added dropwise from the addition funnel so as to maintain the reaction temperature at 100 to 110° C. After completion of the addition, the reaction solution was heated for an additional 1 hour at 120° C. After cooling, the reaction solution was transferred to a pear-shaped evaporating flask and concentrated under reduced pressure on a rotary evaporator to give 61.0 g of a very light brown liquid 103.3 g 1,1,3,3,-tetramethyldisiloxane, 40 mL concentrated hydrochloric acid, 20 mL water, and 20 mL isopropanol were subsequently placed in a 300-mL four-neck flask equipped with a stirrer, thermometer, reflux condenser, and an addition funnel and were stirred. The 61.0 g of the very light brown liquid prepared as described above was then gradually added dropwise from the addition funnel over 1 hour. After the completion of addition, the reaction solution was stirred at room temperature for an additional 1 hour. The reaction solution was then transferred to a separatory funnel, the lower layer was separated off, and the remaining upper layer solution was washed twice with 100 mL water, then once with 100 mL saturated aqueous sodium bicarbonate solution, and finally dried over anhydrous magnesium sulfate. The solids were filtered off and the resulting solution was concentrated under reduced pressure to yield 73.3 g of a colorless and transparent liquid. Analysis of this reaction product by $^{29}$Si-nuclear magnetic resonance analysis confirmed it to be carbosiloxane dendrimer with the average molecular formula given below having an average of 7 silicon-bonded hydrogen atoms and an average of 7 silicon-bonded methoxy groups in each molecule. Using gel permeation chromatography, this carbosiloxane dendrimer was found to have a number-average molecular weight of 2,547 (polystyrene basis) and a dispersity index of 1.71.

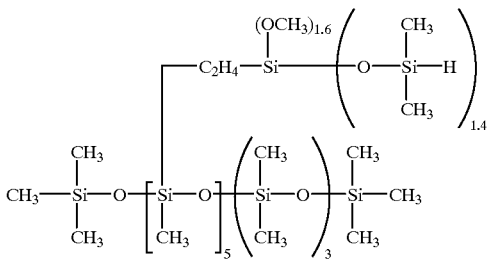

Example 5

160 g vinyltrimethoxysilane and 0.10 g 3% isopropanolic chloroplatinic acid solution were introduced into a 500-mL four-neck flask equipped with a stirrer, thermometer, reflux condenser, and an addition funnel and then heated at 100° C. while stirring. 100 g polysiloxane with the average compositional formula $\{H(CH_3)_2SiO_{1/2}\}_{10}(SiO_{4/2})_5$ was then gradually added dropwise from the addition funnel so as to maintain the reaction temperature at 100 to 110° C. After completion of the addition, the reaction solution was heated for an additional 1 hour at 120° C. After cooling, the reaction solution was concentrated under reduced pressure to give 231 g of a very light brown liquid. 193 g 1,1,3,3,-tetramethyldisiloxane, 86 g acetic acid, and 0.24 g trifluoromethanesulfonic acid were subsequently placed in a 2-L four-neck flask equipped with a stirrer, thermometer, reflux condenser, and an addition funnel and were heated to 50° C. with stirring. 207 g of the very light brown liquid prepared as described above was then gradually added dropwise from the addition funnel over 1 hour. After the completion of addition, the reaction solution was stirred at 50° C. for an additional 1 hour. The reaction solution was subsequently transferred to a separatory funnel, washed twice with 200 mL water, then once with 100 mL saturated aqueous sodium bicarbonate solution, and finally dried over anhydrous magnesium sulfate. The produced solids were filtered off and the resulting solution was concentrated under reduced pressure to yield 308 g of a colorless and transparent liquid. Then, 59.3 g vinyltrimethoxysilane and 0.05 g 3% isopropanolic chloroplatinic acid solution were introduced into a 300-mL four-neck flask equipped with a stirrer, thermometer, reflux condenser, and an addition funnel and heated to 100° C. while stirring. 57.6 g of the colorless, transparent liquid obtained as described above was gradually added dropwise from the addition funnel so as to maintain the reaction temperature at 100 to 110° C. After completion of the addition, the reaction solution was heated for an additional 1 hour at 120° C. After cooling, the reaction solution was concentrated under reduced pressure to give 109 g of a very light brown liquid. Finally, 80.4 g 1,1,3,3,-tetramethyldisiloxane, 36.0 g acetic acid, and 0.11 g trifluoromethanesulfonic acid were placed in a 2-L four-neck flask equipped with a stirrer, thermometer, reflux condenser, and an addition funnel and were heated to 50° C. with stirring. 103 g of the very light brown liquid obtained as described above was then gradually added dropwise from the addition funnel over 1 hour. After the completion of addition, the reaction solution was stirred at 50° C. for an additional 1 hour. The reaction solution was subsequently transferred to a separatory funnel, washed twice with 200 mL water, then once with 100 mL saturated aqueous sodium bicarbonate solution, and finally dried over anhydrous magnesium sulfate. The produced solids were filtered off and the resulting solution was concentrated under reduced pressure to yield 143 g of a colorless and transparent liquid. Analysis of this reaction product by $^{29}$Si-nuclear magnetic resonance analysis confirmed it to be carbosiloxane dendrimer with the average molecular formula given below having an average of 51 silicon-bonded hydrogens in each molecule. Using gel permeation chromatography, this carbosiloxane dendrimer was found to have a number-average molecular weight of 3,381 (polystyrene basis) and a dispersity index of 1.19.

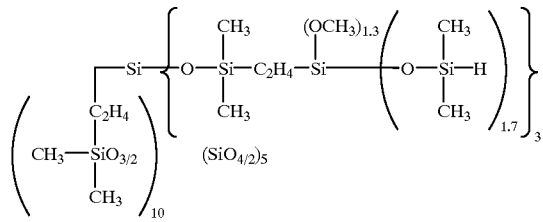

Application Example 1

100 parts organopolysiloxane (viscosity=2,100 centistokes) with the formula

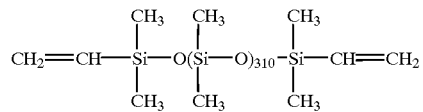

was mixed to homogeneity with 0.49 parts of the SiH-functional carbosiloxane dendrimer prepared in Example 2 with the formula

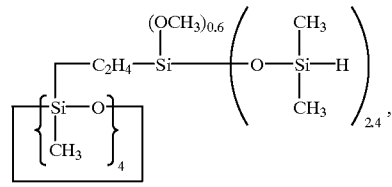

0.1 part of a toluene solution of a platinum/divinyltetramethyldisiloxane complex (platinum concentration=0.5%), and 0.1 part 3-phenyl-1-butyn-3-ol (reaction inhibitor) to give a curable organopolysiloxane composition having a vinyl group silicon-bonded hydrogen molar ratio of 1:1.3. This organopolysiloxane composition was heated at 90° C. in order to measure the cure time. This organopolysiloxane composition was also cured by heating at 90° C. for 20 minutes to give a 2 mm-thick sheet which was submitted to measurement of the tensile strength and durometer. The measured values are reported in Table 1.

Comparative Application Example 1

100 parts organopolysiloxane (viscosity=2,100 centistokes) with the formula

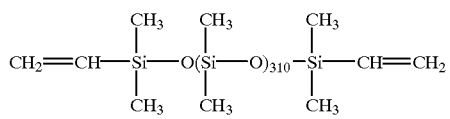

was mixed to homogeneity with 0.84 part SiH-functional methylhydrogenpolysiloxane with the formula

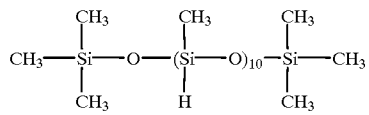

in place of the carbosiloxane dendrimer prepared in Example 2, 0.1 part of a toluene solution of a platinum/divinyltetramethyldisiloxane complex (platinum concentration=0.5%), and 0.1 part 3-phenyl-1-butyn-3-ol (reaction inhibitor) to give a curable organopolysiloxane composition having a vinyl group: silicon-bonded hydrogen molar ratio of 1:1.3. The cure time of the resulting organopolysiloxane composition was measured as in Application Example 1. This organopolysiloxane composition was also cured by heating at 130° C. for 20 minutes to give a 2 mm-thick sheet which was submitted to measurement of the tensile strength and durometer. The measured values are reported in Table 1.

TABLE 1

|  | Application Example 1 | Comparative Application Example 1 |
|---|---|---|
| cure times at 90° C. (min) | | |
| 10% torque increase | 0.5 | 3.2 |
| 90% torque increase | 0.6 | 9.5 |
| physical properties of the cured product | | |
| curing temperature (° C.) | 90 | 130 |
| tensile strength (kg/cm$^2$) | 8 | 2 |
| durometer | 36 | 22 |

The carbosiloxane dendrimer according to the present invention is characterized by a highly branched structure in which the siloxane bond and silalkylene bond alternate, by the presence of silicon-bonded hydrogen and/or silicon-bonded alkoxy in each molecule, and by an excellent reactivity.

Example 6

35.5 g vinyltris(trimethyl)silane and 0.04 g 3% isopropanolic chloroplatinic acid solution were introduced into a 100-mL four-neck flask equipped with a stirrer, thermometer, reflux condenser, and an addition funnel and then heated to 100° C. while stirring. To this was then gradually added 8.2 g tetrakis(dimethylsiloxy)silane dropwise from the addition funnel so as to maintain the reaction temperature at 100° C. After completion of the addition, the reaction solution was heated for an additional 1 hour at 120° C. After cooling, the reaction solution was concentrated under reduced pressure to give 40.5 g of a very light brown liquid. The viscosity of this liquid at 25° C. was 98 CSt, and the glass transition temperature measured by DSC was −85.1° C., and it was confirmed that crystallization usually seen in linear polydimethylsiloxanes does not occur to this liquid. Analysis of this reaction product by $^{29}$Si-nuclear magnetic resonance analysis confirmed it to be carbosiloxane dendrimer with the average molecular formula given below. Using gel permeation chromatography, this carbosiloxane dendrimer was found to have a number-average molecular weight of 2180 (polystyrene basis) and a dispersity index of 1.06.

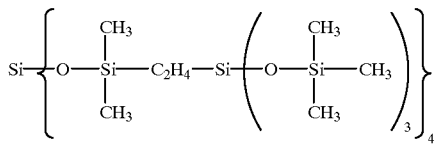

Example 7

107 g vinyltrimethoxysilane and 0.04 g 3% isopropanolic chloroplatinic acid solution were introduced into a 200-mL four-neck flask equipped with a stirrer, thermometer, reflux condenser, and an addition funnel and then heated to 100° C. while stirring. To this was then gradually added 8.2 g tetrakis(dimethylsiloxy)silane dropwise from the addition funnel so as to maintain the reaction temperature at 100° C. After completion of the addition, the reaction solution was heated for an additional 1 hour at 120° C. After cooling, the reaction solution was concentrated under reduced pressure to give 138 g of a very light brown liquid. This was named intermediate A.

80.6 g 1,1,3,3-tetramethyldisiloxane, 72.1 g acetic acid and 0.11 g trifluoromethanesulfonic acid were introduced into a 300-mL four-neck flask equipped with a stirrer, thermometer, reflux condenser, and an addition funnel and then heated to 40° C. while stirring. To this was then gradually added 76.8 g intermediate A (obtained above) dropwise from the addition funnel over one hour. After completion of the addition, the reaction solution was heated for an additional 1 hour at 50° C. The mixture was separated and the bottom layer was discarded. The top layer was then washed twice with 50 ml of water and once with 50 ml of saturated sodium hydrogen carbonate aqueous solution, and was dried over anhydrous sodium sulfate. The solid content was filtered off and the solution was concentrated under vacuum to give 119 g of a colorless transparent liquid. This was named intermediate B.

88.9 g vinyltrimethoxysilane and 0.04 g 3% isopropanolic chloroplatinic acid solution were introduced into a 200-mL four-neck flask equipped with a stirrer, thermometer, reflux condenser, and an addition funnel and then heated to 100° C. while stirring. To this was then gradually added 60.5 g intermediate B dropwise from the addition funnel so as to maintain the reaction temperature at 100° C. After completion of the addition, the reaction solution was heated for an additional 1 hour at 120° C. After cooling, the reaction solution was concentrated under reduced pressure to give 134 g of a very light brown liquid. This was named intermediate C.

75.1 g 1,1,3,3-tetramethyldisiloxane, 53.7 g acetic acid and 66.9 g of intermediate C were introduced into a 300-mL four-neck flask equipped with a stirrer, thermometer, reflux condenser, and an addition funnel and then heated to 50° C. while stirring. The reaction mixture was then added with 0.08 g trifluoromethanesulfonic acid and was stirred at 50° C. for one hour. The mixture was separated and the bottom layer was discarded. The top layer was then washed twice with 30 ml of water and once with 30 ml of saturated sodium hydrogen carbonate aqueous solution, and was dried over anhydrous sodium sulfate. The solid content was filtered off and the solution was concentrated under vacuum to give 77.1 g of a colorless transparent liquid. This was named intermediate D. 46.1 g of polyoxyethylene glycol with one-end allyl functionality (degree of polymerization 12) and 0.07 g 3% isopropanolic chloroplatinic acid solution were introduced into a 100-mL four-neck flask equipped with a stirrer, thermometer, reflux condenser, and an addition funnel and then heated to 80° C. while stirring. To this was then gradually added 15.0 g intermediate D dropwise from the addition funnel so as to maintain the reaction temperature at 85° C. After completion of the addition, the reaction solution was heated for an additional 1 hour at 100° C. After cooling, the reaction solution was concentrated under reduced pressure to give 64.0 g of a very light brown liquid.

Analysis of this reaction product by $^{29}$Si-nuclear magnetic resonance analysis confirmed it to be carbosiloxane dendrimer with the average molecular formula given below. Using gel permeation chromatography, this carbosiloxane dendrimer was found to have a number-average molecular weight of 26030 (polystyrene basis) and a dispersity index of 1.32.

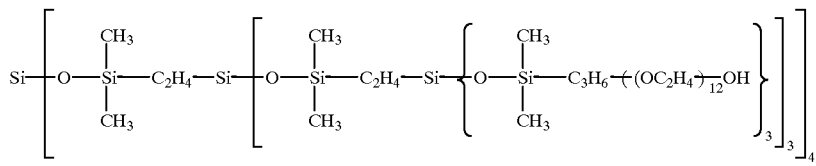

We claim:

1. Carbosiloxane dendrimer that contains at least one siloxane unit with the general formula

$R^1$ is $C_1$ to $C_{10}$ alkyl or aryl, a is an integer from 0 to 2, and $X^1$ is the silylalkyl group with the following formula at i=1

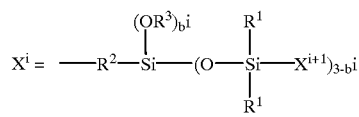

where $R^1$ is $C_1$ to $C_{10}$ alkyl or aryl, $R^2$ is $C_2$ to $C_{10}$ alkylene, $R^3$ is $C_1$ to $C_{10}$ alkyl, $X^{i+1}$ is the hydrogen atom or the above-defined silylalkyl group at i=i+1, i is an integer with a value from 1 to 10 that specifies the generation of the said silylalkyl group, and $b^i$ is an integer from 0 to 3 with the proviso that $b^1$ in at least one $X^1$ in each molecule is an integer from 0 to 2 wherein when more than 1 is present the subject siloxane units may be the same or different, and whose core is a polysiloxane structure that contains at least 2 silicon atoms and the aforesaid siloxane unit(s).

2. The carbosiloxane dendrimer described in claim 1, that contains at least one difunctional siloxane unit with the general formula $R^1_2SiO_{2/2}$ or $X^1R^1SiO_{2/2}$ ($R^1$ and $X^1$ are defined as above) in the polysiloxane structure comprising the core.

3. The carbosiloxane dendrimer described in claim 1, that has the following general formula

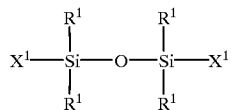

in which $R^1$ and $X^1$ are defined as above.

4. The carbosiloxane dendrimer described in claim 1, wherein the polysiloxane structure comprising the core contains at least 5 silicon atoms and is composed of siloxane units selected from the general formulas $R^1SiO_{3/2}$, $X^1SiO_{3/2}$, $R^1_3SiO_{1/2}$, and $X^1R^1_2SiO_{1/2}$ ($R^1$ and $X^1$ are defined as above).

5. The carbosiloxane dendrimer described in claim 1, wherein the polysiloxane structure comprising the core contains at least 6 silicon atoms and is composed of siloxane units selected from the general formulas $SiO_{4/2}$, $R^1_3SiO_{1/2}$, and $X^1R^1_2SiO_{1/2}$ ($R^1$ and $X^1$ are defined as above).

6. The carbosiloxane dendrimer described in claim 1, whose molecular weight, determined on a polystyrene basis, has a dispersity index no greater than 2.

7. The carbosiloxane dendrimer described in claim 1, wherein said dendrimer is is addition-reacted with a compound containing one non-conjugated alkenyl group in the molecule in the presence of a platinum transition metal catalyst.

8. The carbosiloxane dendrimer described in claim 1, wherein said dendrimer is reacted under acidic conditions with a disiloxane of the general formula

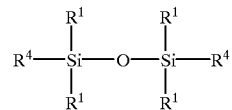

where $R^1$ is $R^1$ is $C_1$ to $C_{10}$ alkyl or aryl, and $R^4$ is independently a $C_2$ to $C_{30}$ hydrocarbon group.

9. The carbosiloxane dendrimer described in claim 1, wherein said dendrimer is is addition-reacted with a compound containing one non-conjugated alkenyl group and at least one atom which is different from carbon or hydrogen or a group containing such an atom in the molecule, or a hydrocarbon containing one non-cunjugated alkenyl group per molecule, in the presence of a platinum transition metal catalyst.

10. The carbosiloxane dendrimer described in claim 1, wherein said dendrimer is reacted under acidic conditions with a disiloxane of the general formula

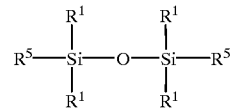

where $R^1$ is $C_1$ to $C_{10}$ alkyl or aryl, and $R^5$ is an unsubsitituted monovalent hydrocarbon group, a monovalent hydrocarbon group substituted by atoms other than carbon and hydrogen, and a monovalent hydrocarbon group substituted by a group that contains atoms other than carbon and hydrogen.

* * * * *